United States Patent [19]

Giordano et al.

[11] 4,244,881

[45] Jan. 13, 1981

[54] PROCESS FOR PREPARING ALPHA-NAPHTHOL ESTERS OF ALIPHATIC CARBOXYLIC ACIDS

[75] Inventors: Claudio Giordano, Novara; Aldo Belli, Intra; Francesco Minisci, Milan, all of Italy

[73] Assignee: Montedison S.p.A., Milan, Italy

[21] Appl. No.: 24,857

[22] Filed: Mar. 28, 1979

[30] Foreign Application Priority Data

Mar. 29, 1978 [IT] Italy ............................... 21717 A/78

[51] Int. Cl.³ .............................................. C07C 67/05
[52] U.S. Cl. .................................. 260/410.5; 560/131
[58] Field of Search ............... 560/139, 130, 131, 138; 260/410.5

[56] References Cited

U.S. PATENT DOCUMENTS

| | | | |
|---|---|---|---|
| 3,424,789 | 1/1969 | Schulz et al. | 568/809 |
| 3,641,136 | 2/1962 | Onopchenko et al. | 562/417 |
| 3,809,715 | 5/1974 | Hanotier | 560/139 |

FOREIGN PATENT DOCUMENTS 2193811  2/1974  France .

OTHER PUBLICATIONS

*Chemical Abstracts*, vol. 67, #64,101z, (1967).
Kirk–Othmer, *Encyclopedia of Chemical Technology*, vol. 13, pp. 700, 717 and 718, 2nd Ed., (1967).
*Beilsteins Handbuch der Organischen Chemie*, (EIII), 4th Ed., vol. VI, pp. 2912–2913, (1966).
Brill, William F., "Terephthalic Acid by Single-Stage Oxidation," Ind. & Eng. Chem., 52, (10), pp. 837–840, (1960).
Heiba, E. I. et al., "Oxidation by Metal Salts, V. Cobaltic Acetate Oxidation of Alkylbenzenes," J. of Am. Chem. Soc., 91, (24), pp. 6830–6837, (1969).

*Primary Examiner*—Natalie Trousof
*Assistant Examiner*—L. Hendriksen

[57] ABSTRACT

Alpha-naphthol esters of aliphatic carboxylic acids are prepared by oxidation of naphthalene in the presence of cobalt compounds.

15 Claims, No Drawings

PROCESS FOR PREPARING ALPHA-NAPHTHOL ESTERS OF ALIPHATIC CARBOXYLIC ACIDS

THE PRIOR ART

It is known that alpha-naphthol esters of the aliphatic carboxylic acids are useful for many purposes. Such esters are useful not only as intermediates for the synthesis of organic compounds in general, but also the alpha-naphthol obtained by conventional hydrolysis of the esters, or of insecticides such as N-methylcarbamate of alpha-naphthyl, etc., are useful in the preparation of dyes and perfumes.

Since the aim of such uses is to prepare so-called "fine chemicals", the degree of purity of the starting product is of particular importance or even critical to the use thereof in the industrial applications. In the case of alpha-naphthol, for instance, the absence of the isomer, beta-naphthol or at least the reduction of the amount thereof mixed with the alpha-isomer to a negligible amount, is of considerable importance. On the other hand, and as is known, it is difficult to separate the two isomers to a sufficient extent by means of the usual industrial methods. That involves, in consequence, the necessity of having recourse to complicated and expensive syntheses to insure a reasonable selectivity of the desired alpha-naphthol isomer.

For example, according to one known process, alpha-naphthol can be prepared by nitration of naphthalene under controlled conditions, reduction of the nitrocompound to naphthylamine, separation of the alpha and beta isomers and, finally, obtaining the alpha-naphthol by acid hydrolysis at high temperature.

According to another known process, alpha-naphthol can be prepared by sulphonation of a naphthalene with 98% sulphuric acid and under mild temperature conditions (temperature about 60° C.), and by successive alkaline hydrolysis under severe conditions (370°–410° C.). It is furthermore obtainable by oxidation of 1-tetralone with sulphur or selenium at high temperatures, or by heterogeneous dehydrogenation with Ni, Pd, Pl.

Clearly, a simpler and more selective method of obtaining alpha-naphthol is of great interest.

Methods of directly oxidizing aromatic compounds in the presence of cobalt compounds are known.

For example, it is known to obtain aromatic acids (terephthalic acid) by oxidizing, in one step, alkylbenzenes (p-xylene) in the presence of acetate of cobalt II and of ketonic activators. Oxidation is selectively directed to the alkyl chains on the aromatic nucleus, while the process is of the auto-catalytic type.

Finally, a process has been described for preparing alpha-naphthol esters of aliphatic carboxylic acids by reaction of naphthalene in the presence of aliphatic carboxylic acids with organic salts of cobalt III in the absence of gaseous oxygen and in an inert atmosphere, under conditions of a narrow concentration of ions of cobalt III: CoIII/CoII>>1, with yields not fully satisfactory with respect to the salt of cobalt III.

THE PRESENT INVENTION

As far as the applicants know, no method has been described so far for preparing alpha-naphthol esters of aliphatic carboxylic acids which includes the selective and direct introduction of an aliphatic acyloxy group on the naphthalene nucleus, using salts of cobalt II and oxygen.

One object of this invention is to provide a simple and economic process for preparing alpha-naphthol esters of aliphatic carboxylic acids, which is free from the drawbacks and disadvantages of the prior art processes.

This and other objects, which to a technician skilled in the art will more clearly appear from the following description, are achieved by the present invention in accordance with which alpha-naphthol esters of aliphatic carboxylic acids are prepared by a process characterized in that naphthalene is reacted with an aliphatic carboxylic acid in a medium consisting of an aliphatic carboxylic acid and in the presence of a system consisting of a saline compound of cobalt II, of a ketone containing at least a methylene group or a methine group in alpha position in respect to the carbonyl group, and of oxygen and/or an oxygen-containing gas, at a temperature ranging from about 70° to about 110° C.

The reaction can be schematically represented by the following equation:

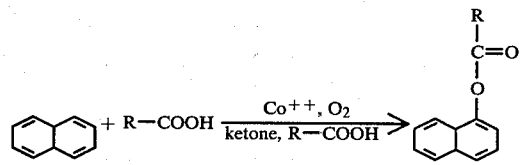

wherein R is an alkyl having up to 10 carbon atoms, and $Co^{++}$ is a Co compound selected from the salts of an organic or an inorganic anion, such as, for example, the aliphatic carboxylic acids, the chloride, the sulphate, the acetylacetonate, etc.

More specifically, the process of this invention consists in reacting naphthalene with an aliphatic carboxylic acid in the presence of a compound of CoII in a medium consisting of an aliphatic carboxylic acid R-COOH, in the presence of an oxidizing system composed of oxygen and/or an oxygen-containing gas and of a ketone.

The indicated behavior of naphthalene in the presence of molecular oxygen is all the more surprising since one skilled in the art would have reasonably expected, under the conditions described hereinabove, an important, if not even a predominant, oxidation of naphthalene to secondary compounds, (naphthoquinone, phthalic acid, etc.).

According to this invention, oxygen and/or gases containing it, preferably air, are used as oxidizing gas. Advantageous results are obtained, for example, by using oxygen amounts varying from 60 to 600 liters/hour per mole of the cobalt II compound, or corresponding amounts of air.

The compound of cobalt II, according to this invention, is a salt of an inorganic anion (chloride, sulphate, etc.), of an organic anion of carboxylic acids R-COOH (acetate, propionate, etc.) or an enolate (acetylacetonate, etc.). In a presently preferred embodiment, it is the salt of the same aliphatic acid R-COOH used as reagent, or mixtures thereof, in which R has the meaning stated hereinabove.

Advantageous results are attained by using anhydrous and/or hydrated cobaltous acetate, propionate, acetylacetonate, chloride, sulphate, etc.

If an inorganic salt of Co II (chloride, etc.) is employed, the reaction is promoted by the presence of alkaline acetates or of buffering agents in general, examples of which include sodium or potassium acetate.

The compound of cobalt II is utilized in an initial molar ratio of the compound of cobalt II to naphthalene of from about 10:1 to about 1:10, preferably from about 2:1 to about 1:2. The initial concentration of the compound of cobalt II is advantageously adjusted to an initial value varying from 0.2 to 0.5 mole of CoII per liter of reacting mass.

The reaction temperature is comprised between about 70° and 110° C., temperatures around 90° C. being preferred.

The reaction is conducted in a medium consisting of an aliphatic carboxylic acid of formula R-COOH as defined hereinabove. Preferably, it is the same acid used to form the salt of cobalt II, or mixtures thereof.

Usually, the process of this invention is carried out at atmospheric pressure.

The ketone which is part of the ketone/oxygen oxidizing system consists of a ketone containing in its structure at least a methylene or methine group ($>$CH—) in alpha position with respect to the carbonyl group, and is an aliphatic, cycloaliphatic or aliphatic-aromatic ketone. Ketones which have proved effective in the practice of this invention include ethylmethylketone, diethylketone, cyclohexanone, propiophenone and methylisopropylketone. The ketones are used in a molar ratio to the compound of Co II ranging from about 4:1 to about 8:1.

The reaction, after a variable induction period, as a function of the temperature, etc., and of from about 30 minutes to 1 hour, starts in a moderately exothermic way and terminates in about 2-6 hours.

Illustratively, the process of this invention is conducted as follows:

The salt (acetate) of cobalt II, the naphthalene and the aliphatic carboxylic acid (acetic acid) are introduced, in the desired ratios, into a reactor equipped with stirrer, thermometer, cooler, and charging and gas introducing systems. Successively, oxygen is bubbled in under stirring, then the mass is heated to about 90° C. and the ketone (ethylmethyl ketone) is introduced. After an initial induction time (from 45 minutes to 1 hour), a moderately exothermic reaction starts and the temperature is adjusted at 90°-93° C. for about 4 hours on the whole. After cooling to room temperature, the naphthol ester (acetate) is separated by extraction, and is washed etc., according to conventional methods.

The process, due to the mild and simple operating conditions, is particularly advantageous.

A further advantage consists in the high selectivity and in the exclusive obtainment of an alpha-naphthol of such a degree of purity as to allow its direct use without further purification to separate beta-isomer from it.

The following examples are given to illustrate the invention in more detail, and are not intended to be limiting.

Example 14 is a comparative example which was carried out in the absence of ketone from the catalytic system.

EXAMPLE 1

To a reactor consisting of a 250-ml flask equipped with a mechanical agitator, a thermometer, a cooler, a plunging pipe for gas bubbing and a feeding funnel, and containing a solution of

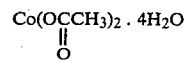

(14.94 g; 0.06 mole) and of naphthalene (10.24 g; 0.08 mole) in glacial acetic acid (150-ml) there were added, in 5 minutes 36 g or 0.5 moles of 2-butanone.

The mass was maintained at 90° C. and under intense stirring (1100 rpm) in an oxygen stream (10 l/hr).

The reaction mixture was then kept at 90° C., under strong, intense stirring and in an oxygen stream for 4 hours. During the first two hours, the color of the solution changed from violet to dark green, and the color change was accompanied by a slight exothermicity of the reaction.

The reaction mass was cooled to room temperature, poured into water and extracted with ethyl ether. The ether extracts were gathered and washed, first with water, then with a sodium bicarbonate-saturated solution, and finally dried.

By gas-chromatographic analysis of the raw (total) reaction product so obtained it was determined that 19.6% of the fed naphthalene was converted to alpha-acetoxynaphthalene. The gas chromatographic and nuclear magnetic resonance analyses carried out on the raw reaction product revealed that β-acetoxynaphthalene was absent.

2.26 g of α-naphthol ($15.7 \times 10^{-3}$ moles) were obtained by hydrolysis of the raw reaction product.

EXAMPLE 2

Example 1 was repeated except that a reduced amount of naphthalene (5.12 g; 0.04 mole) was used for a shorter reaction time (2 hours and 30 minutes).

The gas-chromatographic analysis of the raw reaction product revealed that 33.7% of the fed naphthalene was converted to α-acetoxynaphthalene. β-acetoxynaphthalene was absent.

EXAMPLE 3

Example 1 was repeated but using a reduced amount of 2-butanone (18 g; 0.25 mole).

From the gas-chromatographic analysis (G.L.C.) of the raw reaction product, it appeared that 18.5% of the fed naphthalene was converted to α-acetoxynaphthalene. β-acetoxynaphthalene was absent.

EXAMPLE 4

Example 1 was repeated but using a reduced amount of 2-butanone (9 g; 0.125 mole).

The G.L.C. analysis of the raw reaction product revealed that 11% of the fed naphthalene was converted to α-acetoxynaphthalene. β-acetoxynaphthalene was absent.

EXAMPLE 5

Example 1 was repeated but at a higher temperature (105° C.) and with a shorter reaction time (3 hours).

The G.L.C. analysis of the raw reaction product revealed that 10% of the fed naphthalene was converted to α-acetoxynaphthalene.

EXAMPLE 6

Example 1 was repeated but employing a higher oxygen flow (20 l/h).

From the G.L.C. analysis of the raw reaction product, it resulted that 21.3% of the fed naphthalene was converted to α-acetoxynaphthalene.

EXAMPLE 7

Example 1 was repeated but using a lower oxygen flow (5 liters/hour).

From the G.L.C. analysis of the reaction product it appeared that 14.4% of the fed naphthalene was converted to α-acetoxynaphthalene.

EXAMPLE 8

Example 1 was repeated but using 3-pentanone (42 g; 0.5 mole) instead of 2-butanone, and employing a shorter reaction time (3 hours and 30 minutes).

The G.L.C. analysis of the raw reaction product revealed that 29% of the fed naphthalene was converted to α-acetoxynaphthalene.

EXAMPLE 9

Example 1 was repeated, but using phenylethyl ketone (67 g; 0.5 mole) instead of 2-butanone and employing a longer reaction time (5 hours and 30 minutes).

From the G.L.C. analysis of the raw reaction product it appeared that 14% of the fed naphthalene was converted to α-acetoxynaphthalene.

EXAMPLE 10

Example 1 was repeated, but using cyclohexanone (23.5 g; 0.24 mole) instead of 2-butanone, and employing a lower temperature (70° C.) and a shorter reaction time (3 hours).

The G.L.C. analysis of the raw reaction product revealed that 3% of the fed naphthalene was converted to α-acetoxynaphthalene.

EXAMPLE 11

Example 1 was repeated, but using

(10.62 g; 0.06 mole) instead of

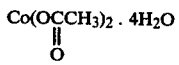

and employing a longer reaction time (4 hours and 30 minutes).

From the G.L.C. analysis of the raw reaction product, it resulted that 23.5% of the fed naphthalene was converted to α-acetoxynaphthalene.

EXAMPLE 12

Example 1 was repeated, but using propionic acid (150 ml) instead of acetic acid.

The G.L.C. analysis of the raw reaction product revealed that 2.2% of the fed naphthalene was converted to α-naphthylpropionate.

EXAMPLE 13

Example 1 was repeated, but using 3-methyl-2-butanone (43 g; 0.5 mole) instead of 2-butanone, and employing a lower temperature (70° C.) and a longer reaction time (9 hours and 30 minutes).

The G.L.C. analysis of the raw reaction product revealed that 6.2% of the fed naphthalene was converted to α-acetoxynaphthalene.

EXAMPLE 14 (Comparative Test)

By way of comparison, Example 1 was repeated but in the absence of ketones and for a longer reaction time (8 hours).

The G.L.C. analysis of the raw reaction product revealed that less than 1% of the fed naphthalene was converted to α-acetoxynaphthalene.

EXAMPLE 15

It was operated as described in Example 1, but using air instead of oxygen and with a higher flow (30 liters/hour).

From the G.L.C. analysis of the raw reaction product, it appeared that 5.5% of the fed naphthalene was converted to α-acetoxynaphthalene.

EXAMPLE 16

It was operated as in Example 1, but using $CoCl_2 \cdot 6H_2O$ instead of

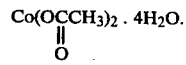

The G.L.C. analysis of the raw reaction product revealed that 3.5% of the fed naphthalene was converted to α-acetoxynaphthalene.

EXAMPLE 17

It was operated as in Example 1 in the presence of potassium acetate (11.76 g; 0.12 mole).

The G.L.C. analysis of the raw reaction product revealed that 13% of the fed naphthalene was converted to α-acetoxynaphthalene.

What we claim is:

1. A process for preparing alpha-naphthol esters of aliphatic carboxylic acids by reaction of naphthalene with aliphatic carboxylic acids, characterized in that naphthalene is reacted with an aliphatic carboxylic acid in a medium consisting of an aliphatic carboxylic acid and in the presence of a system composed of a compound of cobalt II selected from the group consisting of cobalt enolate, cobalt salts of inorganic anions, and cobalt salts of organic anions of aliphatic carboxylic acids R-COOH in which R is an alkyl group containing up to 10 carbon atoms; of a ketone containing in its structure at least a methylene or methine group in alpha position with respect to the carbonyl group; and of oxygen, at a temperature of from about 70° to about 110° C.

2. The process of claim 1, in which the medium is an aliphatic carboxylic acid R-COOH, wherein R is an alkyl having up to 10 carbon atoms.

3. The process of claim 2, in which the aliphatic carboxylic acid R-COOH used as medium is the aliphatic carboxylic acid used to form the salt of the cobalt II.

4. The process of claim 1, in which air is used as the oxygen source.

5. The process of claim 1, in which the compound of cobalt II is the anhydrous or hydrated acetate, propionate, chloride, sulphate or acetylacetonate.

6. The process of claim 1, in which the cobalt II compound is used in an initial molar ratio with respect to the naphthalene ranging from about 10:1 to 1:10.

7. The process of claim 1, in which the cobalt II compound is used in an initial molar ratio, with respect to the naphthalene, of from about 2:1 to 1:2.

8. The process of claim 1, in which the initial concentration of the cobalt II compound is from about 0.2 to 0.5 mole/liter.

9. The process of claim 1, in which the temperature is maintained at about 90° C.

10. The process of claim 1, in which the oxygen flow and/or the flow of the gas containing it ranges from 60 to 600 liter/hour of $O_2$ per mole of cobalt II.

11. The process of claim 1, in which the ketone containing in its structure a methylene or methine group in alpha position with respect to the carbonyl group is an aliphatic, cycloaliphatic or aliphatic-aromatic ketone.

12. The process of claim 11, in which the ketone is ethylmethyl ketone, diethyl ketone, cyclohexanone, propiophenone or methylisopropyl ketone.

13. The process of claim 1, in which the ketone is introduced in a molar ratio to the initial cobalt compound ranging from about 4:1 to about 8:1.

14. The process of claim 1, in which the inorganic salt of Co II is employed associated with buffering agents.

15. The process of claim 14, in which the buffering agent is sodium or potassium acetate.

* * * * *